United States Patent [19]

Tsuzuki et al.

[11] Patent Number: 5,278,158
[45] Date of Patent: Jan. 11, 1994

[54] OXAZINOBENZAZOLE COMPOUNDS

[75] Inventors: Ryuji Tsuzuki; Yuzo Matsumoto; Akira Matsuhisa; Toru Yoden; Wataru Uchida, all of Ibaraki; Isao Yanagisawa, Tokyo, all of Japan

[73] Assignee: Yamanouchi Pharmaceutical Co., Ltd., Tokyo, Japan

[21] Appl. No.: 837,252

[22] Filed: Feb. 14, 1992

[30] Foreign Application Priority Data

Feb. 18, 1991 [JP] Japan .................................. 3-109918
Jul. 18, 1991 [JP] Japan .................................. 3-269939

[51] Int. Cl.$^5$ .................. A61K 31/535; C07D 498/04
[52] U.S. Cl. .................................. 514/229.8; 544/101
[58] Field of Search ............................ 544/101, 229.8

[56] References Cited

U.S. PATENT DOCUMENTS

4,446,113  5/1984  Evans et al. ........................ 422/267
4,661,482  4/1987  Nedelec et al. ..................... 544/101

FOREIGN PATENT DOCUMENTS

0076075  4/1983  European Pat. Off. .
58-67683  4/1983  Japan .

*Primary Examiner*—Cecilia Tsang
*Assistant Examiner*—Philip I. Datlow
*Attorney, Agent, or Firm*—Burgess, Ryan & Wayne

[57] ABSTRACT

Oxazinobenzazole derivatives represented by the formula (I):

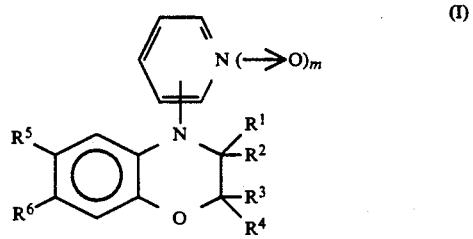

wherein $R^1$, $R^2$, $R^3$ and $R^4$, which may be the same or different, each independently represents a hydrogen atom or a lower alkyl group; $R^5$ and $R^6$ jointly form, in conjunction with the two adjacent carbon atoms, a substituted or unsubstituted 5- or 6-membered heterocyclic ring having at least two nitrogen atoms and optionally having one or more heteroatom(s) selected from the group consisting of an oxygen atom, a sulphur atom and a nitrogen atom; and m is an integer of 0 or 1, and pharmaceutically acceptable salts thereof. The compounds of the present invention are useful as antispasmodic medicaments.

4 Claims, No Drawings

OXAZINOBENZAZOLE COMPOUNDS

FIELD OF THE INVENTION

This invention relates to novel oxazinobenzazole derivatives or pharmaceutically acceptable salts thereof, which are useful as drugs, in particular, as a K+ channel activating agent and pharmaceutical compositions containing the same as well as to intermediates for the production of these derivatives and salts.

The oxazinobenzazole derivatives of this invention and salts thereof are novel compounds which serve to activate the K+ channels, thereby exhibiting the antispasmodic action (the action of relaxing the smooth muscles).

BACKGROUND OF THE INVENTION

As the smooth-muscle relaxants, are known two types of drugs: those acting upon the contractile system, and those acting upon the relaxing system. As typical examples of the former type, may be mentioned various blockers with the excitatory, chemical transmitter receptor and calcium antagonists, and as those of the latter type, may be mentioned stimulants with the inhibitory, chemical transmitter receptor and nitrate drugs (nitric acid esters).

Recently, drugs which relax smooth muscles by activating the K+ channels have been reported as new smooth muscle relaxants.

The K+ channels in thick arteries (such as coronary and cerebral arteries) and in the tracheal smooth muscles are more rapidly and powerfully activated, compared with those in general excitatory tissues, thus functioning to prevent excessive excitation of these tissues (maintenance of the inside diameters of these arteries). However, once their physiological functions are damaged, these K+ channels suffer from electrical excitation similarly to general excitatory tissues, thus locally generating high contractile tension (spasm). The spasm generated in the coronary artery, the cerebral artery and bronchial smooth muscles are said to cause diseases such as angina pectoris, cerebrovascular diseases and asthma, and K+ channel activating agents are considered to be useful for the treatment and prevention of these diseases.

As compounds having K+ channel opening activity are known 4-(2-oxo-1-pyrrolidinyl)-2H-1-benzopyran-3-ol derivatives disclosed in JP-A-58-67683 (the term "JP-A" as used herein means an "unexamined published Japanese patent application"). The compounds of this invention are novel oxazinobenzazole derivatives which are different from the above compounds in structure and exhibit more powerful action of activating the K+channels.

SUMMARY OF THE INVENTION

As a result of continuous studies on compounds activating the K+ channels, the present inventors discovered that novel oxazinobenzoxadiazole, oxazinobenzothiadiazole and oxazinobenzotriazole derivatives represented by the general formula (I), as well as salts thereof, are effective for this purpose. This invention was accomplished on the basis of this finding.

Thus, this invention provides oxazinobenzazole derivatives represented by the following general formula (I):

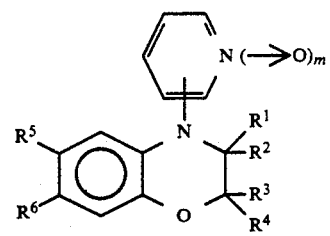

(wherein $R^1$, $R^2$, $R^3$ and $R^4$, which may be the same or different, each independently represents a hydrogen atom or a lower alkyl group; $R^5$ and $R^6$ jointly form, in conjunction with the two adjacent carbon atoms, a substituted or unsubstituted 5- or 6-membered heterocyclic ring having at least two nitrogen atoms and optionally having one or more heteroatom(s) selected from the group consisting of an oxygen atom, a sulphur atom and a nitrogen atom; and m is an integer of 0 or 1, or a pharmaceutically acceptable salts thereof, as well as the pharmaceutical compositions containing the same.

This invention also provides valuable intermediates for the production of the present compound (I), such as 2-(7-amino-3,4-dihydro-2,2-dimethyl-6-nitro-2H-1,4-benzoxazin-4-yl)pyridine N-oxide or salts thereof; 2-(6-amino-3,4-dihydro-2,2-dimethyl-7-nitro-2H-1,4-benzoxazin-4-yl)pyridine N-oxide or salts thereof; and 7,8-dihydro-6,6-dimethyl-6H-[1,2,5]oxadiazolo[3,4-g][1,4]benzoxazine or salts thereof.

DETAILED DESCRIPTION OF THE INVENTION

Described below are the compounds (I) in more detail.

The term "lower" used in the definition of the general formulas in this specification means, unless otherwise specified, a linear or branched carbon chain with a carbon number of 1 to 6.

Accordingly, as examples of the "lower alkyl group" may be mentioned methyl, ethyl, propyl, isopropyl, propyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups.

As preferred examples of the heterocyclic ring formed by $R^5$ and $R^6$ taken jointly, may be mentioned the ones shown below.

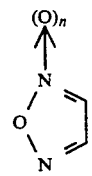

(wherein n 1 is 0 (not N oxide) or 1 (N-oxide), and the same applies hereinafter),

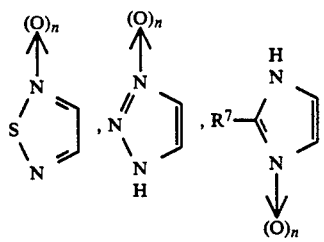

(wherein R⁷ is a hydrogen atom, a hydroxyl group or a lower alkyl group),

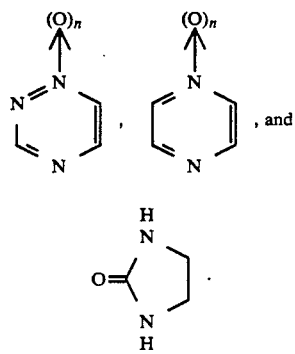

It is known that N-oxide of an oxadiazole derivative may exist as tautomeric isomers as shown below. In addition, the compounds of this invention may contain one or more asymmetric carbon atom(s) depending on the kinds of substituents.

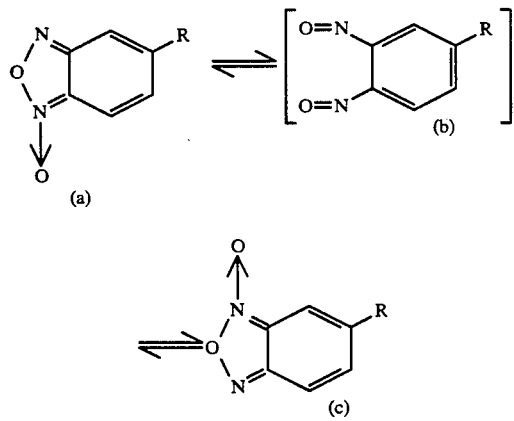

Accordingly, the compounds of this invention also include tautomeric isomers and stereoisomers.

Furthermore, the compounds of this invention may form acid addition salts, such as salts with mineral acids (e.g., hydrochloric, hydrobromic, hydroiodic, sulfuric, nitric and phosphoric acids), salts with organic acids (e.g., formic, acetic, propionic, oxalic, malonic, succinic, fumaric, maleic, malic, tartaric, methanesulfonic and ethanesulfonic acids) and salts with acidic amino acids (e.g., aspartic and glutamic acids).

The compounds of this invention can be prepared by utilizing various synthetic methods. Typical examples of these synthetic methods are shown below.

Preparative Method 1

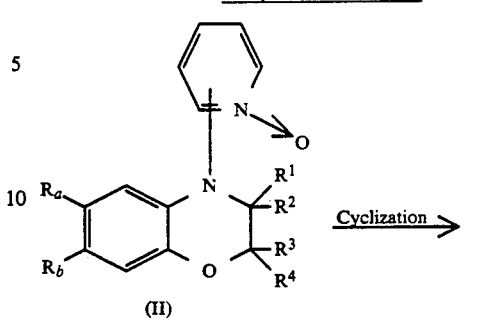

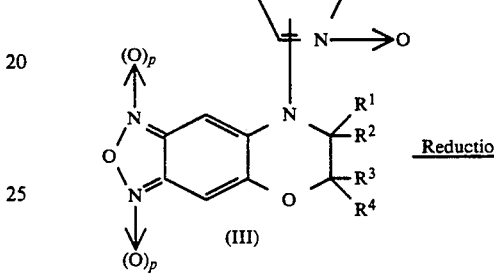

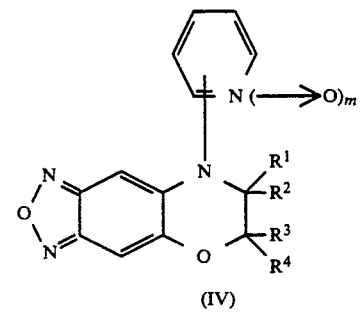

(wherein either one of the $R_a$ and $R_b$ groups is an amino group and the other is a nitro group; $R^1$ through $R^4$ and m are as defined above; and either one of the two p values is 0 and the other is 1.)

Of the compounds (I) of this invention, the ones represented by the general formula (IV) can be prepared by cyclizing a compound (II) to form a compound (III), followed by reduction.

The cyclizing reaction of the first step may be performed by adding dropwise an aqueous solution of sodium hypochlorite to a compound (II) in water, methanol, ethanol or a mixture thereof at room temperature or under cooling, or by the reaction of at least equimolar amount of iodobenzene diacetate with a compound (II) in a solvent inert to the reaction, such as benzene and toluene, at room temperature or under heating.

Alternatively, the cyclization may be carried out by reaction of a compound (II) with at least equimolar amounts of sodium nitrite and sodium azide in that order in an acidic aqueous solution, and cyclizing the precipitate thus obtained by heating in a solvent inert to the reaction, such as benzene and toluene.

The reducing reaction of the second step may be performed by the method commonly employed for the deoxygenation of N-oxides; by the reaction of a deoxygenating reagent exemplified by a trivalent phosphorus compound, such as triethyl phosphite, triphenyl phosphite, tributylphosphine and phosphorus trichloride, with a compound (III) in the absence of solvent or in a solvent inert to the reaction, such as benzene, toluene, xylene, diethyl ether, chloroform, ethyl acetate and diethylene glycol diethyl ether, at room temperature or under heating.

Preparative Method 2

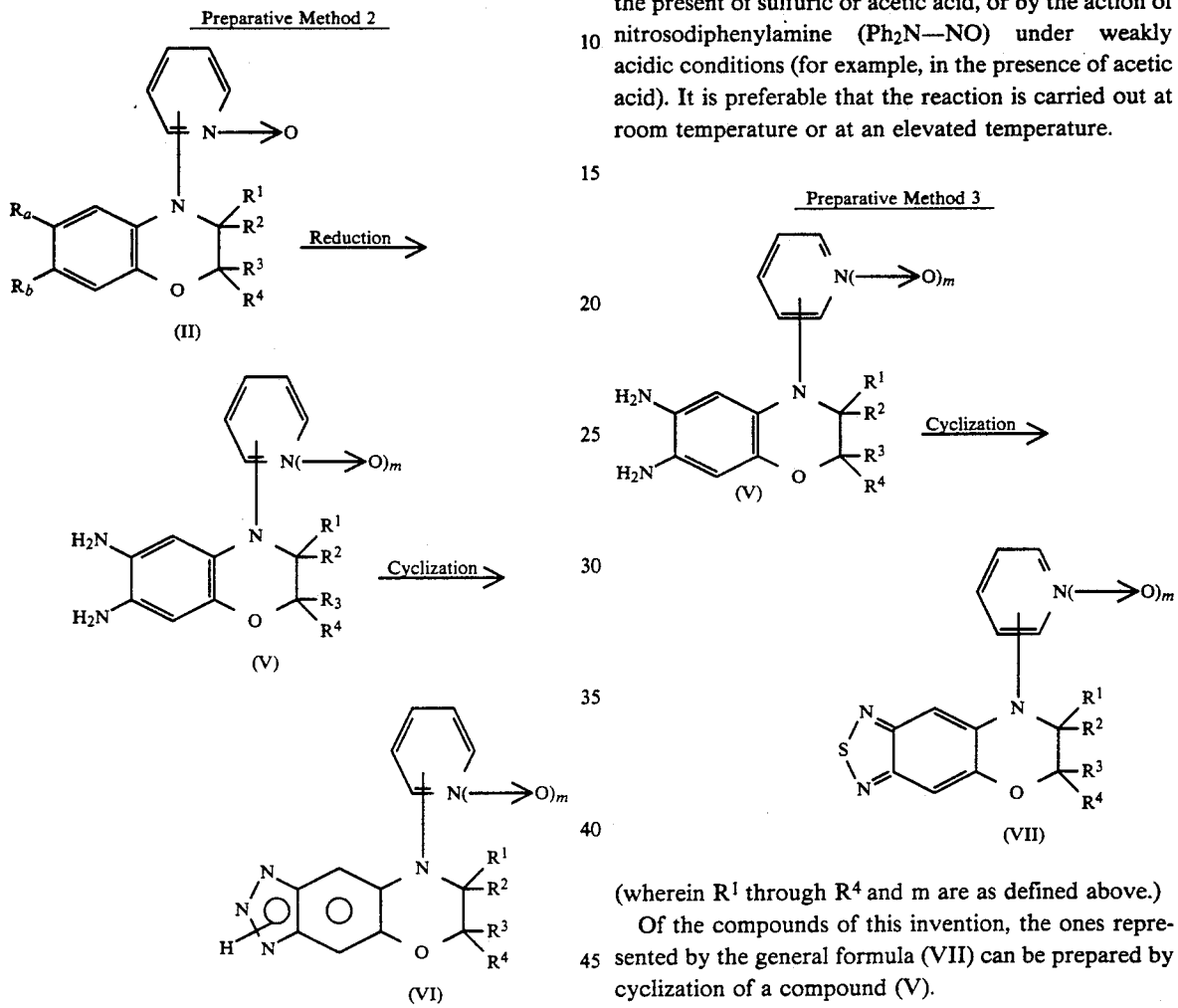

(wherein $R_a$, $R_b$, $R^1$ through $R^4$ and m are as defined above.)

Of the compounds of this invention, the ones represented by the general formula (VI) can be prepared by reduction of a compound (II) to form a compound (V), followed by cyclization.

The reducing reaction of the first step may be performed by a method commonly employed for the reduction of nitro group; for example, by the catalytic hydrogenation using palladium-carbon powder or Raney-nickel catalyst, or by the reduction using zinc powder, iron powder or lithium aluminum hydride. In these reducing reactions, it is possible to selectively reduce the nitro group alone and to perform also the deoxygenation of the N-oxide radical by properly selecting reaction conditions. When the compound (V) thus formed is unstable, it is preferable to immediately use the crude product for the succeeding step without isolation and purification.

The cyclizing reaction of the second step can be effected by the method commonly employed for the formation of diazonium salt; reaction of sodium nitrite with the compound (V) in the presence of an inorganic acid, such as hydrochloric and sulfuric acids, or an organic acid, such as acetic acid, followed by heating (or heating under reflux) to effet cyclization. This reaction may also be effected by the action of nitrous acid in the present of sulfuric or acetic acid, or by the action of nitrosodiphenylamine ($Ph_2N$—NO) under weakly acidic conditions (for example, in the presence of acetic acid). It is preferable that the reaction is carried out at room temperature or at an elevated temperature.

Preparative Method 3

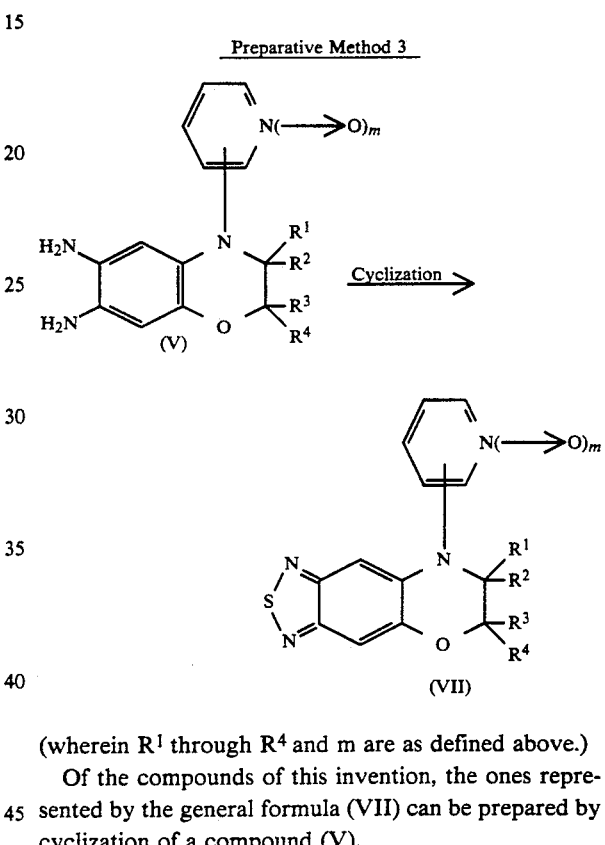

(wherein $R^1$ through $R^4$ and m are as defined above.)

Of the compounds of this invention, the ones represented by the general formula (VII) can be prepared by cyclization of a compound (V).

This cyclizing reaction can be effected by the action of thionyl chloride in a solvent, such as benzene, toluene, chloroform, methylene chloride and 1,2-dichloroethane, in the presence of a base, such as pyridine and triethylamine.

Preparative Method 4

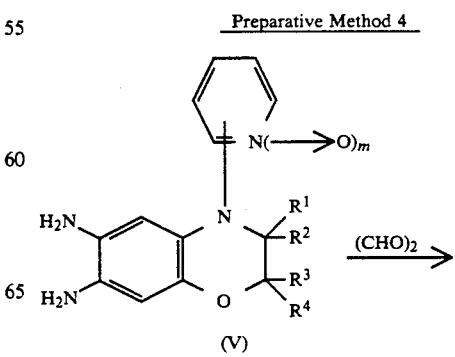

-continued
Preparative Method 4

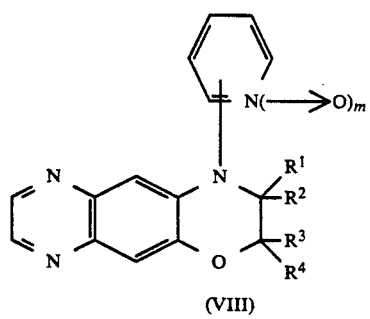

(wherein $R^1$ through $R^4$ and m are as defined above.)

The objective compounds having oxazino [2,3-g]quinoxaline ring represented by the formula (VIII) can be prepared by cyclic condensation between a diamino compound (V) and glyoxal. This reaction is carried out by the action of at least equimolar amount of glyoxal (as an aqueous solution) upon the diamino compound in a solvent, such as water, ethanol and acetic acid, under ice cooling, at room temperature or under heating. The presence of sodium bisulfite or other catalyst in the reaction system is preferably to accelerate the reaction.

Preparative Method 5

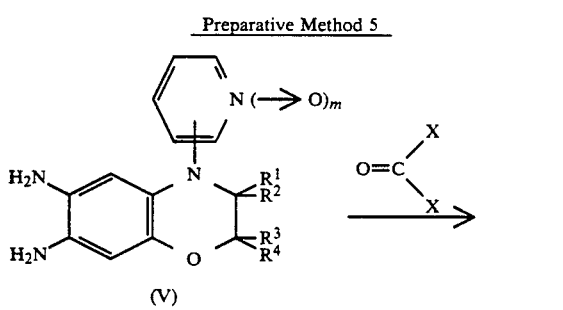

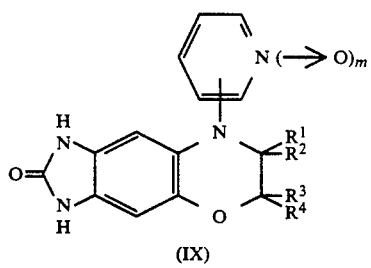

(wherein X is a halogen atom, an imidazol-1-yl group or a phenoxy group; and $R^1$ through $R^4$ and m are as defined above.)

The objective compounds having oxazino [2,3-f]benzimidazoline ring represented by the formula (IX) can be prepared by the reaction between a diamino compound (V) and at least equimolar amount of a highly reactive, carbonic acid derivative in an inert solvent, such as benzene, toluene, methylene chloride, chloroform, diethyl ether and tetrahydrofuran. As examples of the carbonic acid derivative, may be mentioned phosgene, diphenyl carbonate, N,N'-carbonyldiimidazole and p-nitrophenyl chloroformate. It is preferable to add a base, such as triethylamine, pyridine, potassium carbonate and sodium hydroxide, to the reaction system, and the reaction is carried out at room temperature or under heating.

Preparative Method 6

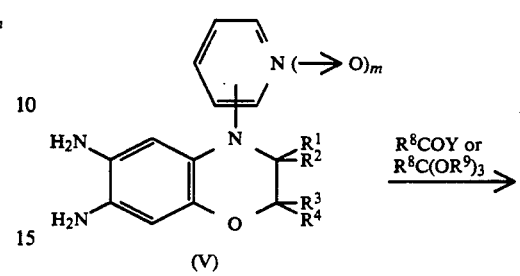

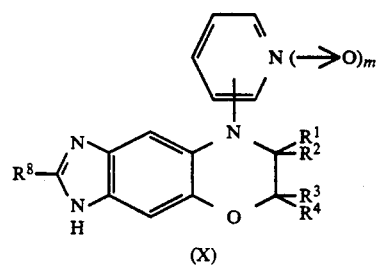

(wherein $R^8$ is a hydrogen atom or an alkyl group; $R^9$ is an alkyl group; Y is a hydroxyl group, a halogen atom, an alkoxy group or an acyloxy group; and $R^1$ through $R^4$ and m are as defined above.)

The compounds having imidazo [4,5-g]benzoxazine ring represented by the formula (X) can be prepared by the reaction between a diamino compound (V) and at least equimolar amount of a carboxylic acid or a reactive derivative thereof in the absence of solvent or in an inert solvent, such as benzene, toluene, xylene, diethyl ether, dimethylformamide, methylene chloride and chloroform. As examples of the carboxylic acid derivative, may be mentioned an acid halide, an acid anhydride and an ortho ester. This reaction should preferably be carried out at an elevated temperature or by heating under reflux. When an excessive amount of formic acid is used as the carboxylic acid, deoxygenation of the N-oxide group may also proceed simultaneously depending on the reaction conditions adopted.

Preparative Method 7

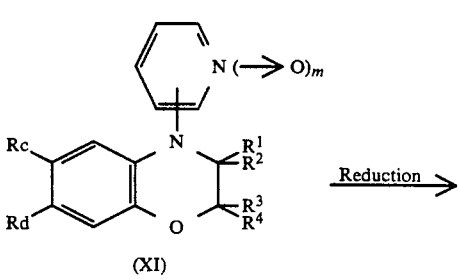

-continued
Preparative Method 7

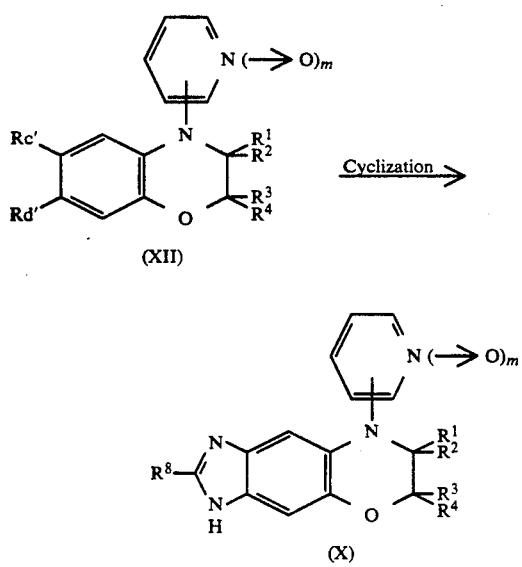

(XII)

(X)

(wherein either one of $R_c$ and $R_d$ groups is a nitro group and the other is a group of the formula $R^8CONH-$; either one of $R_c'$ and $R_d'$ groups is an amino group and the other is a group of the formula $R^8CONH-$ (in which $R^8$ is as defined above); and $R^1$ through $R^4$ and m are as defined above.)

This method is an alternate method of Preparative Method 6 described above.

The reducing reaction of the first step may be carried out in the same way as in Preparative Method 2. The cyclizing reaction of the second step is effected by heating the acylamino compound (XII) thus formed in the absence of solvent or in a solvent, such as benzene, toluene, xylene and ethanol, in the presence of a dehydrating agent, such as polyphosphoric acid and sulfuric acid in some cases.

The acylamino compound (XII) formed by the first-step reaction may be isolated, or the reaction mixture may be used as such for the succeeding reaction.

Preparative Method 8

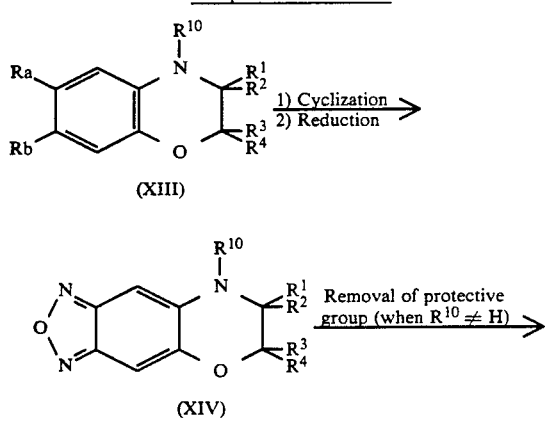

(XIII)

(XIV)

-continued
Preparative Method 8

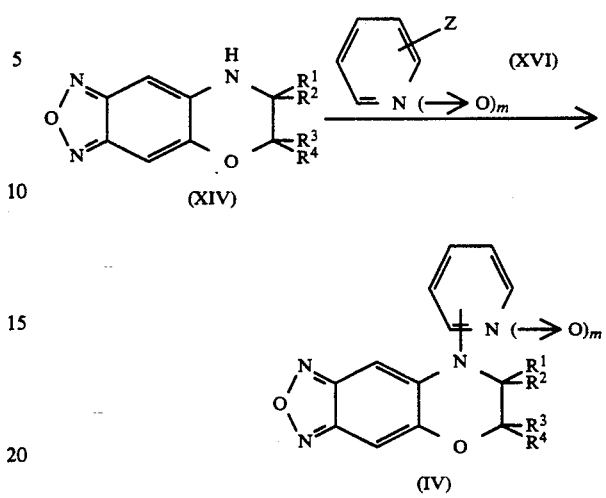

(XIV)

(IV)

(wherein $R^{10}$ is a hydrogen atom or a protective group of an amino group; Z is a leaving group; and $R^1$ through $R^4$, $R_a$, $R_b$, and m are as defined above.)

This method is an alternate method of Preparative Method 1 described above, and can be carried out by cyclizing and reducing a compound of formula (XIII) to form a compound of formula (XIV), then removing the protective group $R^{10}$, when $R^{10}$ is not an hydrogen atom, to form a compound of formula (XV), and condensing the compound of formula (XV) with a compound of formula (XVI). The cyclizing reaction and the reducing reaction can be effected in the same way as in Preparative Method 1.

Removal of the $R^{10}$ group may be carried out by a method suitable for the type of the protective group used.

The condensation can be effected by reaction of a compound of formula (XV) with a compound of formula (XVI) in a solvent inert to the reaction, such as dimethyl sulfoxide, dimethylformamide, hexamethylphosphoramide and tetrahydrofuran, in the presence of a base, such as triethylamine, potassium hydride, sodium hydride, potassium t-butoxide and potassium carbonate.

As the protective group $R^{10}$, may be used any groups commonly employed for the amino-group protection that remain stable in the reactions of synthesizing the compound (XIII) and of producing the compound (XIV) from the compound (XIII), such as acetyl, chloroacetyl, trifluoroacetyl, benzoyl, benzyloxycarbonyl, t-butoxycarbonyl, benzyl and phenylsulfonyl groups.

As examples of the leaving group Z, may be mentioned hydroxy group, alkoxy groups, acyloxy groups, methylsulfonyloxy group, p-toluenesulfonyloxy group, halogen atoms, and alkylthio groups. Of these, halogen atoms are the most preferred.

The products formed by the reactions described above can be easily isolated and purified. In each case, the reaction mixture is poured into an excessive amount of water or ice water, the organic substances contained in the resulting mixture are extracted with a proper organic solvent, such as methylene chloride, chloroform, benzene, diethyl ether and ethyl acetate, the extract is dehydrated, the solvent is distilled off from the dried solution (under reduced pressure), and the residue thus obtained is purified by recrystallization or column chromatography on silica gel. As examples of the solvent used for the recrystallization and column chromatography, may be mentioned hexane, benzene, methylene chloride, chloroform, ethyl acetate, acetone, ethanol, methanol and mixtures thereof.

In some cases, the product formed separates out as crystals as the reaction proceeds, where the crystals are collected by filtration and recrystallized from a proper solvent mentioned above, thus ensuring simpler isolation and purification.

As described above, some of the compounds of this invention exist as various types of stereoisomers. Of these, geometric isomers can be isolated and purified by utilizing the difference in physicochemical properties; and optical isomers can be isolated and purified by using a proper starting material or by applying a method of separating a racemic body commonly employed (for example, formation of diastereomeric salts with an optically active acid (e.g., tartaric acid), followed by optical resolution).

The compounds offered by the present invention exhibit $K^+$ channel opening activity and are therefore useful for the prevention and treatment of ischemic diseases (angina pectoris and myocardial infarction etc.), hypertension (arteriosclerosis, obesity and hyperlipemia etc.), and cardiovascular diseases (such as congestive heart failure, arrhythmia, and peripheral vascular disorders etc.).

In addition, the compounds of the present invention are also useful for the prevention and treatment of other diseases caused by the contraction of smooth muscles, such as cerebrovascular diseases (e.g., cerebrovascular spasm, megrim and dizziness), peripheral vascular diseases (e.g., hair growth disorders, alopecia, feeling of the cold in the limbs), respiratory diseases (e.g. reversible airway obstruction, hypersensitive airway obstruction and asthma), gastrointestinal diseases (e.g., ulcers, neurogenic gastrointestinal disorders, irritable colon syndrome, diseases of the diverticulum, and biliary obstruction), visual and auditory disorders (e.g., abnormality in the inner ear, abnormality in the auditory organs, glaucoma, amblyopia, and intraocular hypertension), urinary tract diseases (e.g., renal failure, disorders caused by the movement of renal calculi, pollakiuria, dysuria, and incontinence), and genital organ diseases (e.g., premature delivery and menstrual disorders). Furthermore, the compounds of the present invention are also useful for treatment of diseases caused by abnormal level of blood sugar (e.g., hypoglycemia, and diabetes) and those caused by abnormality of the cardiac conduction system (e.g., arrhythmia).

The above-mentioned pharmacological effects of the compounds of the present invention may be demonstrated by the test methods described below. The $K^+$ channel opening action was observed at a test sample concentration in the range from $10^{-9}$ to $10^{-4}$M in the isolated tissues. The compounds, when administered intravenously, reduced the blood pressure and increased the coronary artery blood flow in the dose range from 1 to 1000 μg/Kg and, when injected into the coronary artery, they dilated the coronary artery in the dose range from 0.3 to 100 μg. It was also demonstrated that some of the compounds of this invention possess the long-lasting hypotensive and coronary vasodilating effects.

The test methods for supporting the pharmacological effects of several compounds among the compounds according to the present invention are described below.

Test Methods (1) Effects on 3,4-Diaminopyridine Induced Rhythmic Contractions

The experiment was carried out according to the method of Uchida, Sugimoto, et al. (Myakkangaku, 24, 133–143, 1984). Mongrel dogs of either sex were anesthetized with intravenous administration of 30 mg/Kg pentobarbital and were sacrificed by bleeding and then, the heart was excised from each animal. In the Krebs-Henseleit solution, the left circumflex branch or the anterior descending branch was isolated and cut into rings about 2 mm in width. The ring segments were fixed to a stainless-steal hook, and suspended in 37° C. Krebs-Henseleit solution aerated with a mixed gas (95% $O_2$ and 5% $CO_2$) under a tension load of 1.0 g, and isometric contractions were recorded. After the specimen was stabilized for 30 minutes, and rhythmic contractions were induced by treatment with 10 mM 3,4-diamiopyridine. After the amplitude and frequency of rhythmic contractions became substantially steady, a test compound was cumulatively added to the nutritious solution, and the concentration-response curves for the amplitude and frequency of the contractions were constructed and efficacy was evaluated.

$IC_5$ values (the concentrations required to inhibit the frequency of the rhythmic contractions) of the compounds of this invention are between 0.1 and 10 μM.

The test result (the inhibitory effect on the frequency of the rhythmic contractions) is shown in Table 1 below.

TABLE 1

|  | $IC_{50}$ (μM) | $IC_{100}$ (μM) |
|---|---|---|
| Example 1 compound of U.S. Pat. No. 4,446,113 | 0.4 | 7.1 |
| The compounds of this invention: |  |  |
| Example 2 | 0.15 | 0.66 |
| Example 4 | 0.17 | 1.23 |

(2) Effects on the Cardiovascular Systems

Mongrel dogs of either sex were anesthetized with intravenous administration of 30 mg/Kg pentobarbital, and after tracheal intubation, the experiments were performed under artificial respiration. After thoracotomy, heart rate, blood pressure, left ventricle pressure, max. dLVP/dt, pulmonary artery pressure, central venous pressure, cardiac output and the coronary artery blood flow were measured. The effects of test compound on these parameters were evaluated by administering it through the cannula indwelt in the femoral vein. The present compounds are effective for lowering blood pressure at a dose of 1 to 1000 μg/kg i.v.

The test result (mean blood pressure-lowering effect) is shown in Table 2 below.

TABLE 2

|  | MBP (μg/kq i.v. (Δ%)) |
|---|---|
| Example 1 compound of U.S. Pat. No. 4,446,113 | 10 (−29) |
| The compounds of this invention: |  |
| Example 2 | 10 (−33) |
| Example 4 | 10 (−10) |

(3) Coronary Vasodilating Effect

Mongrel dogs of either sex were anesthetized with intravenous administration of 30 mg/Kg pentobarbital.

After tracheal intubation, the experiments was conducted under artificial respiration. After thoracotomy, the left circumflex branch was perfused with the autologous blood derived from the carotid artery at a constant pressure through an extracorporeal circuit. Coronary blood flow was measured with an electromagnetic flow probe installed in the extra-corporeal circuit. The test compound was administered directly into the coronary artery through the extra-corporeal circuit and the coronary vasodilating effects were evaluated.

The dilating action was expressed as percentage with the action of 300 μg papaverine being set as 100%, and the dose required to produce a blood flow increase of 100% ($ED_{100pap}$) was calculated.

The test result is shown in Table 3 below.

TABLE 3

|  | $ED_{100PAP}$ (μg i.a) |
|---|---|
| Example 1 compound of U.S. Pat. No. 4,446,113 | 3.3 |
| Example 2 of this invention: | 3.5 |

(4) Hypotensive Effect

Spontaneously hypertensive rats (SHR) of Okamoto-Aoki strain were anesthetized with pentobarbital, 60 mg/kg i.p. Then, a cannula for blood pressure measurement was indwelt in the left common carotid artery and the other end of the cannula was led out extracorporeally from the posterior neck. After a stabilization period of 4–5 days, blood pressure and heart rate were measured under freely moving condition.

The test compound was suspended in 0.5% methylcellulose solution and the suspension was orally administered in a volume of 5 ml/Kg and the efficacy was evaluated.

The test result is shown in Table 4 below.

TABLE 4

|  | Dose (μg/Kg p.o.) | MBP (Δ%) |
|---|---|---|
| Example 1 compound of U.S. Pat. No. 4,446,113 | 300 | −35 |
| Example 2 of this invention: | 300 | −45 |

The compounds of this invention have low toxicity, and are suitable for drugs. For example, the compound of Example 2 was administered orally to Fischer 344 rats (7 week old; each 5 male and female rats) at 200 mg/kg/day during 2 weeks, and as a result, no rat died.

Pharmaceuticals containing, as an active ingredient, at least one kind of the compounds of this invention or salts thereof can be prepared, by using a carrier, an excipient and other additives commonly employed, in the form of tablets, buccals, powders, beadlets, granules, capsules, pills, solutions for oral administration (including syrup), injections, inhalants, suppositories, solutions for percutaneous administration, ointments, plasters for percutaneous administration, plasters for transmucosal administration (e.g., plasters to be applied in the mouth) and solutions for transmucosal administration (e.g., solutions to be applied to the nose). These are orally or parenterally administered.

As examples of the nontoxic medicinal substance (solid and liquid) used for the carrier and excipient, may be mentioned lactose, magnesium stearate, starch, talc, gelatin, agar, pectin, gum arabic, olive oil, sesame oil, cacao butter, ethylene glycol and other commonly employed materials.

The clinical dosage of the compounds of this invention should be properly set depending on the illness conditions, body weight, age, sex and other factors of the patient to be treated, as well as the route of administration, but is generally 0.1 to 300 mg/day when orally administered to adults and 0.06 to 100 mg/day when intravenously administered, which may be applied at a time or subdivided in two to four doses.

The following Examples will further illustrate the invention.

Some of the starting materials used therein are novel compounds, and the methods for preparing these novel compounds are described in Reference Examples.

Unless otherwise indicated, the ratios used hereinafter are by volume.

REFERENCE EXAMPLE 1

Preparative Method For the Starting Material Used in Example 1

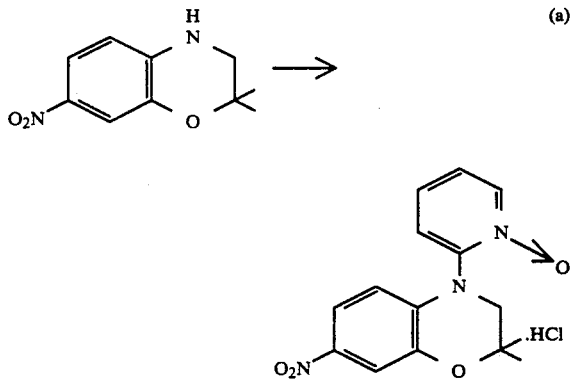

(a)

To a suspension of 0.38 g sodium hydride (60% in paraffin composition) in 14 ml dimethylformamide, was added 1.00 g 3,4-dihydro-2,2-dimethyl-7-nitro-2H-1,4-benzoxazine, and 1.01 g 2-bromopyridine N-oxide hydrochloride was further added under ice-cooling, and the mixture was stirred for 16 hours at 70° C. The reaction mixture was poured to ice water, the resulting mixture was extracted with ethyl acetate, and the extract was washed with an aqueous solution of sodium chloride and dried over anhydrous magnesium sulfate. The solvent was distilled off from the dried solution under reduced pressure, the residue was subjected to column chromatography on silica gel, and elution was conducted by the use of a 3:1 mixture of chloroform and acetone, thus giving 0.34 g of 2-(3,4-dihydro-2,2-dimethyl-7-nitro-2H-1,4-benzoxazin-4-yl)pyridine N-oxide. Ethanolic solution of hydrogen chloride (a mixture of 1 ml concentrated hydrochloric acid and 5 ml ethanol) was then added to the product obtained above, the solvent was distilled off from the mixture, and the residue was recrystallized from acetone, thus giving 182 mg of 2-(3,4-dihydro-2,2-dimethyl-7-nitro-2H-1,4-benzoxazin-4-yl)pyridine N-oxide hydrochloride.

This compound has the physicochemical properties as shown below.

i) Melting point 146°–191° C.

ii) Elemental analysis (as C₁₅H₁₅N₃O₄.HCl)

|  | C (%) | H (%) | N (%) | Cl (%) |
|---|---|---|---|---|
| Calcd. | 53.34 | 4.77 | 12.44 | 10.50 |
| Found | 52.63 | 4.68 | 12.25 | 10.42 | iii) NMR spectrum (DMSO-d₆): δ(ppm): 1.36 (6H, s), 3.70 (2H, s), 6.45 (1H, m), 7.3–7.8 (5H, m), 8.46 (1H, dd), 9.49 (1H, brs)

(b)

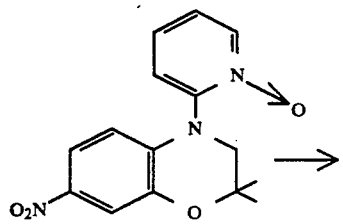

→

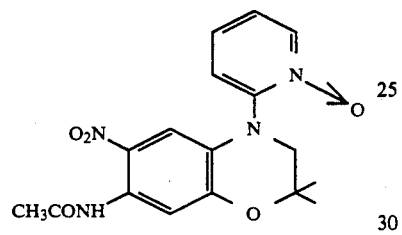

→

1) To a mixture of 8.05 g 2-(3,4-dihydro-2,2-dimethyl-7-nitro-2H-1,4-benzoxazin-4-yl)pyridine N-oxide, 28.50 g ammonium chloride, 140 ml methanol and 140 ml water, was added 34.94 g zinc powder under ice cooling, and the resulting mixture was stirred at 5° C. for 14 hours. The insoluble matters were filtered off from the reaction mixture, the filtrate was concentrated, the concentrate was extracted with ethyl acetate, the extract was dried over anhydrous magnesium sulfate, and the solvents were distilled off form the dried solution, giving 7.32 g of crude 2-(7-amino-3,4-dihydro-2,2-dimethyl-2H-1,4-benzoxazin-4-yl)pyridine N-oxide.

2) To a solution of 6.72 g 2-(7-amino-3,4-dihydro-2,2-dimethyl-2H-1,4-benzoxazin-4-yl)pyridine N-oxide obtained above in 30 ml methylene chloride, was added 2.6 ml acetic anhydride under ice cooling, the mixture was stirred at room temperature for four hours, 20 ml methanol was added to the reaction mixture to decompose the excessive acetic anhydride, and the solvents were distilled off, thus giving 8.40 g of crude 2-(7-acetamido-3,4-dihydro-2,2-dimethyl-2H-1,4-benzoxazin-4-yl)pyridine N-oxide.

3) To a solution of 8.76 g 2-(7-acetamido-3,4-dihydro-2,2-dimethyl-2H-1,4-benzoxazin-4-yl)pyridine N-oxide obtained above in 35 ml acetic acid, was added dropwise a solution of nitric acid in acetic acid (a mixture of 1.49 ml fuming nitric acid and 16 ml acetic acid) under ice cooling, the mixture was stirred at room temperature for one hour, the reaction mixture was poured to ice water, and the resulting mixture was extracted with ethyl acetate. The extract was washed with water and dried over anhydrous magnesium sulfate, the solvents were distilled off from the dried solution, and the residue was subjected to column chromatography on silica gel. The crystals obtained by elution with a 1:1 mixture of chloroform and acetone was recrystallized from 40 ml ethanol, thus giving 5.10 g of 2-(7-acetamido-3,4-dihydro-2,2-dimethyl-6-nitro-2H-1,4-benzoxazin-4-yl)pyridine N-oxide.

This compound has the physicochemical properties as shown below.

i) Melting point 140°–144° C.

ii) Elemental analysis (as C₁₇H₁₈N₄O₅.0.5C₂H₅OH)

|  | C (%) | H (%) | N (%) |
|---|---|---|---|
| Calcd. | 56.98 | 5.06 | 15.63 |
| Found | 56.69 | 5.51 | 14.70 | iii) NMR spectrum (CDCl₃): δ(ppm): 1.42 (6H, s), 2.26 (3H, s), 3.68 (2H, s), 7.0–7.4 (3H, m), 7.48 (1H, s), 8.2–8.4 (1H, m), 8.32 (1H, s), 10.41 (1H, brs)

(c)

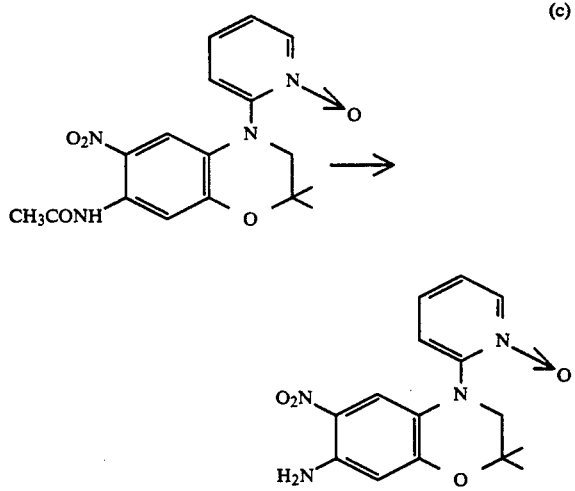

To a suspension of 0.50 g 2-(7-acetamido-3,4-dihydro-2,2-dimethyl-6-nitro-2H-1,4-benzoxazin-4-yl)pyridine N-oxide in 6 ml ethanol, was added 6 ml of 5N HCl, the mixture was stirred at 100° C. for two hours, the reaction mixture was poured to ice water, and the resulting mixture was neutralized with sodium bicarbonate and extracted with chloroform. The extract was dried over anhydrous magnesium sulfate, the solvents were distilled off from the dried solution, and the residue thus obtained was recrystallized from ethanol, thus giving 359 mg of 2-(7-amino-3,4-dihydro-2,2-dimethyl-6-nitro-2H-1,4-benzoxazin-4-yl)pyridine N-oxide.

This compound has the physicochemical properties as shown below.

i) Melting point 285°–289° C. (dec.)

ii) Elemental analysis (as C₁₅H₁₆N₄O₄)

|  | C (%) | H (%) | N (%) |
|---|---|---|---|
| Calcd. | 56.96 | 5.10 | 17.71 |
| Found | 56.80 | 5.15 | 17.50 | iii) NMR spectrum (DMSO-d₆): δ(ppm): 1.35 (6H, s), 3.63 (2H, s), 6.42 (1H, s), 6.85 (1H, s), 7.1–7.3 (3H, m), 7.39 (1H, dd), 7.56 (1H, d), 8.33 (1H, d)

REFERENCE EXAMPLE 2

Preparative Method for the Starting Material Used in Example 4

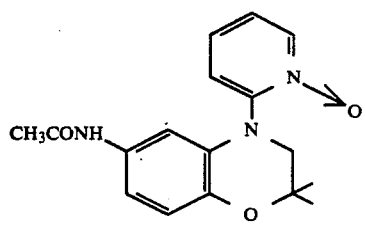
(a)

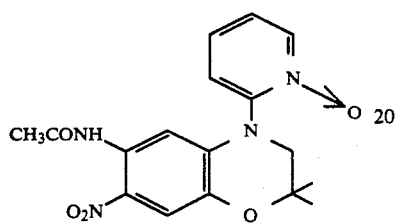

2-(6-Acetamido-3,4-dihydro-2,2-dimethyl-7-nitro-2H-1,4-benzoxazin-4-yl)pyridine N-oxide was obtained from 2-(6-acetamido-3,4-dihydro-2,2-dimethyl-2H-1,4-benzoxazin-4-yl)pyridine N-oxide in the same way as in (b)-(3) of Reference Example 1.

This compound has the physicochemical properties as shown below.

i) Melting point 230°-233° C.
ii) Elemental analysis (as $C_{17}H_{18}N_4O_5 \cdot 0.1H_2O$)

|  | C (%) | H (%) | N (%) |
|---|---|---|---|
| Calcd. | 56.69 | 5.09 | 15.56 |
| Found | 56.61 | 5.06 | 15.61 | iii) Mass spectrometric analysis (m/z): 358 (M+)
iv) NMR spectrum (CDCl$_3$): δ(ppm): 1.43 (6H, s), 2.17 (3H, s), 3.66 (2H, br), 7.2-7.5 (4H, m), 7.79 (1H, s), 7.98 (1H, s), 8.3-8.4 (1H, m), 10.51 (1H, brs)

(b)
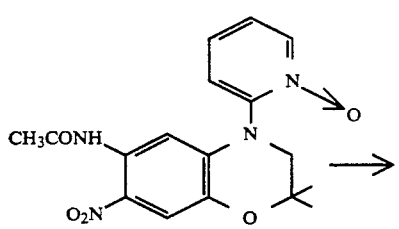

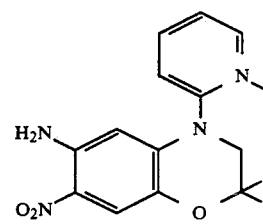

2-(6-Amino-3,4-dihydro-2,2-dimethyl-7-nitro-2H-1,4-benzoxazin-4-yl)pyridine N-oxide was obtained from 2-(6-acetamido-3,4-dihydro-2,2-dimethyl-7-nitro-2H-1,4-benzoxazin-4-yl)pyridine N-oxide in the same way as in (c) of Reference Example 1.

This compound has the physicochemical properties as shown below.

i) Melting point 234°-238° C.
ii) Elemental analysis (as $C_{15}H_{14}N_4O_4$)

|  | C (%) | H (%) | N (%) |
|---|---|---|---|
| Calcd. | 56.96 | 5.10 | 17.71 |
| Found | 56.75 | 5.14 | 17.67 | iii) Mass spectrometric analysis (m/z): 317 (M++1, FAB)
iv) NMR spectrum (DMSO-d$_6$): δ(ppm): 1.34 (6H, s), 3.54 (2H, br), 5.73 (1H, s), 7.02 (2H, br), 7.31 (1H, s), 7.31-7.74 (3H, m), 8.36-8.45 (1H, m)

EXAMPLE 1

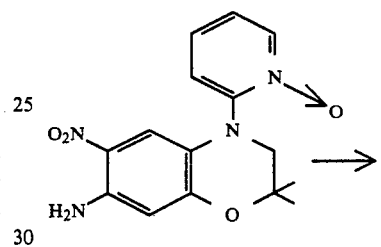

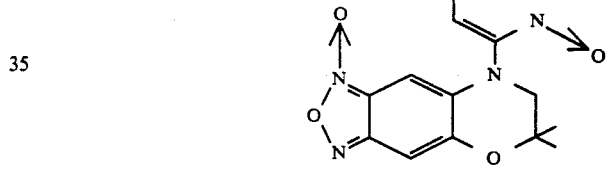

To a mixture of 1.58 g 2-(7-amino-3,4-dihydro-2,2-dimethyl-6-nitro-2H-1,4-benzoxazin-4-yl)pyridine N-oxide, 110 ml ethanol, 8.5 ml 1N aqueous solution of sodium hydroxide and 2.5 ml water, was added dropwise slowly 4.5 ml solution of sodium hypochlorite (a commercially available product with 5% or more of available chlorine) at room temperature, and the mixture was stirred for 15 minutes. The reaction mixture was poured into ice water, the resulting mixture was extracted with ethyl acetate, the extract was washed with an aqueous solution of sodium chloride and dried over anhydrous magnesium sulfate, and the solvent was distilled off from the dried solution. The residue thus obtained was subjected to column chromatography on silica gel, and elution was conducted by the use of a 2:1 mixture of chloroform and acetone, thus giving 751 mg of 7,8-dihydro-6,6-dimethyl-8-(2'-pyridyl)-6H-[1,4]oxazino[2,3-f][2,1,3]benzoxadiazole 1,1'-dioxide. This was further recrystallized from ethanol, giving the sample for elemental analysis.

This compound has the physicochemical properties as shown below.

i) Melting point 197.5-199.5° C. (dec.)
ii) Elemental analysis (as $C_{15}H_{14}N_4O_4$)

|  | C (%) | H (%) | N (%) |
|---|---|---|---|
| Calcd. | 57.32 | 4.49 | 17.83 |

| | C (%) | H (%) | N (%) |
|---|---|---|---|
| Found | 57.16 | 4.58 | 17.64 | iii) NMR spectrum (CDCl₃): δ(ppm): 1.49 (6H, s), 3.2–4.2 (2H, brs), 5.97 (1H, s), 6.74 (1H, s), 7.2–7.6 (3H, m), 8.2–8.4 (1H, m)

EXAMPLE 2

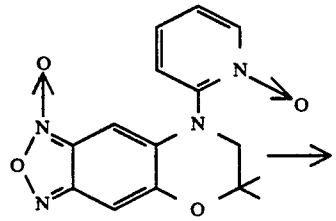

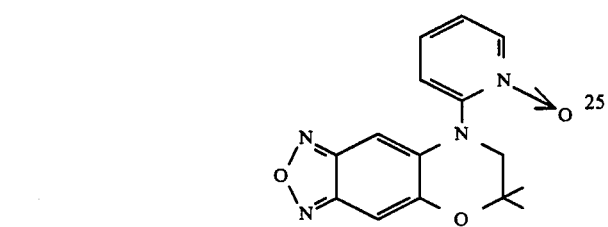

To a suspension of 751 mg 7,8-dihydro-6,6-dimethyl-8-(2'pyridyl)-6H-[1,4]oxazino[2,3-f][2,1,3]-benzoxadiazole 1,1'-dioxide obtained in Example 1 in 15 ml benzene, was added dropwise 0.46 ml triethyl phosphite, and the mixture was heated under reflux for 11 hours with stirring. The solvent was distilled off from the reaction mixture, the residue was subjected to column chromatography on silica gel, and the crystals obtained by elution with a 1:1 mixture of chloroform and acetone was recrystallized from ethanol, giving 312 mg of 2-(7,8-dihydro-6,6-dimethyl-6H-[1,4]oxazino[2,3-f][2,1,3]benzoxadiazol-8-yl)pyridine N-oxide.

This compound has the physicochemical properties as shown below.

i) Melting point 202.5°–205.5° C.
ii) Elemental analysis (as C₁₅H₁₄N₄O₃)

| | C (%) | H (%) | N (%) |
|---|---|---|---|
| Calcd. | 60.40 | 4.73 | 18.78 |
| Found | 60.45 | 4.79 | 18.73 |

NMR spectrum (CDCl₃): δ(ppm): 1.51 (6H, s), 3.2–4.0 (2H, brs), 6.40 (1H, s), 7.05 (1H, s), 7.2–7.6 (3H, m), 8.3–8.4 (1H, m)

EXAMPLE 3

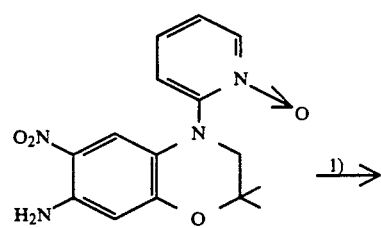

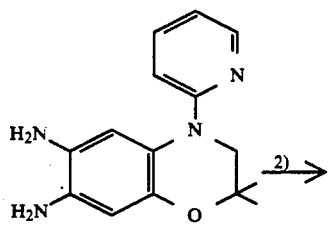

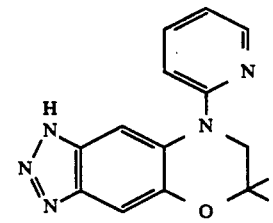

1) To a suspension of 948 mg 2-(7-amino-3,4-dihydro-2,2-dimethyl-6-nitro-2H-1,4-benzoxazin-4-yl)pyridine N-oxide in 180 ml ethanol, was added a catalytic amount of 10% palladium-carbon powder, and catalytic hydrogenation was performed at ordinary temperature and pressure. The catalyst was filtered off from the reaction mixture, and the solvent was distilled off from the filtrate, thus giving crude 6,7-diamino-3,4-dihydro-2,2-dimethyl-4-(2-pyridyl)-2H-1,4-benzoxazine. This product was immediately used for the succeeding reaction.

2) To a solution of 6,7-diamino-3,4-dihydro-2,2-dimethyl-4-(2-pyridyl)-2H-1,4-benzoxazine obtained above in a mixture of 0.84 ml acetic acid and 1.56 ml water, was added a solution of 240 mg sodium nitrite in 1 ml water at room temperature, the mixture was heated at 80° C. for one minute, and a solution of 0.90 g sodium hydroxide and 27 g sodium chloride in 120 ml water was added to the reaction mixture, followed by extraction with ethyl acetate. The extract was washed with water and dried over anhydrous magnesium sulfate, and the solvent was distilled off from the dried solution. The residue left was subjected to column chromatography on silica gel, and the crystals obtained by elution with a 6:1 mixture of chloroform and acetone were recrystallized from ethanol, thus giving 445 mg of 7,8-dihydro-6,6-dimethyl-8-(2-pyridyl)-6H-[1,4]oxazino[2,3-f]benzotriazole.

This compound has the physicochemical properties as shown below.

i) Melting point 224.5°—227.5° C.
ii) Elemental analysis (as C₁₅H₁₅N₅O₂)

| | C (%) | H (%) | N (%) |
|---|---|---|---|
| Calcd. | 63.82 | 5.49 | 24.57 |
| Found | 64.04 | 5.37 | 24.90 | iii) NMR spectrum (CDCl₃+DMSO-d₆): δ(ppm): 1.33 (6H, s), 3.91 (2H, s), 6.7–8.1 (5H, m), 8.33 (1H, d) 14.76 (1H, brs)

EXAMPLE 4

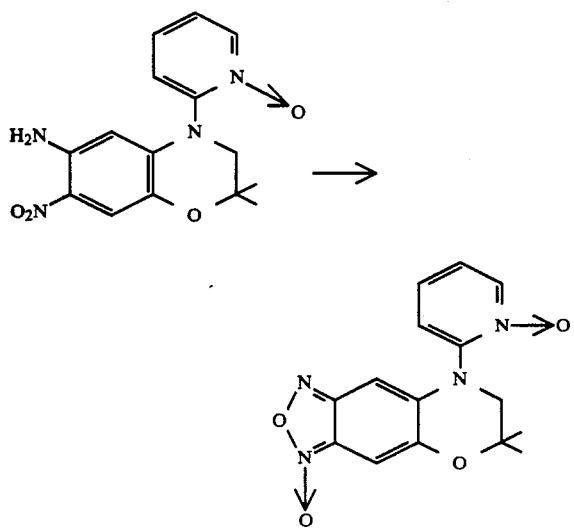

7,8-Dihydro-6,6-dimethyl-8-(2'-pyridyl)-6H-[1,4]oxazino[2,3-f][2,1,3]benzoxadiazole 3,1'-dioxide was obtained from 2-(6-amino-3,4-dihydro-2,2-dimethyl-7-nitro-2H-1,4-benzoxazin-4-yl)pyridine N-oxide in the same way as in Example 1.

This compound has the physicochemical properties as shown below.

i) Melting point 207°–209° C.

ii) NMR spectrum (CDCl₃): δ(ppm): 1.51 (3H, s), 3.64 (2H, brs), 6.03 (1H, s), 6.79 (1H, s), 7.3–7.5 (3H, m), 8.3–8.4 (1H, m)

iii) Mass spectrometric analysis (m/z): 315 (M⁺+1)

EXAMPLE 5

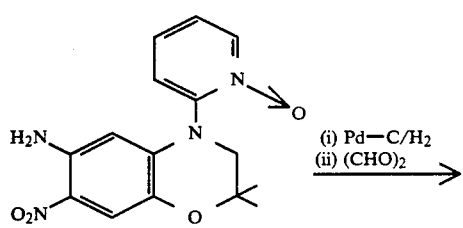

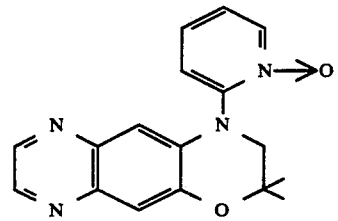

To a solution of 632 mg 2-[6-amino-3,4-dihydro-2,2 dimethyl-7-nitro-2H-1,4-benzoxazin-4-yl)pyridine 1-oxide in 20 ml acetic acid, was added 60 mg of 10% palladium-carbon, and catalytic hydrogenation was performed. The reaction mixture was filtered by the used of Celite, the solvent was distilled off from the filtrate under reduced pressure, the residue was dissolved in 12 ml water, a mixture of 0.6 ml ammonia water, 600 mg sodium bisulfite and 415 ml 40% aqueous solution of glyoxal was added, and the resulting mixture was stirred at room temperature for 20 minutes. The reaction mixture was extracted with chloroform, the extract was washed with water and dried over anhydrous magnesium sulfate, the solvent was distilled off from the dried solution under reduced pressure, and the crude crystals thus obtained were recrystallized from ethanol, giving 150 mg of 2-(8,9-dihydro-7,7-dimethyl-7H-[1,4]oxazino[2,3-g]quinoxalin-9-yl)pyridine 1-oxide.

This compound has the physicochemical properties as shown below.

i) Melting point 228°–230° C.

ii) Elemental analysis (as C₁₇H₁₆N₄O₂)

| | C (%) | H (%) | N (%) |
|---|---|---|---|
| Calcd. | 66.22 | 5.23 | 18.17 |
| Found | 66.00 | 5.31 | 17.90 | iii) NMR spectrum (CDCl₃): δ(ppm): 1.52 (6H, s), 3.78 (2H, brs), 7.12 (1H, s), 7.2–7.4 (2H, m), 7.5–7.7 (2H, m) 8.3–8.4 (1H, m), 8.5–8.7 (2H, m)

EXAMPLE 6

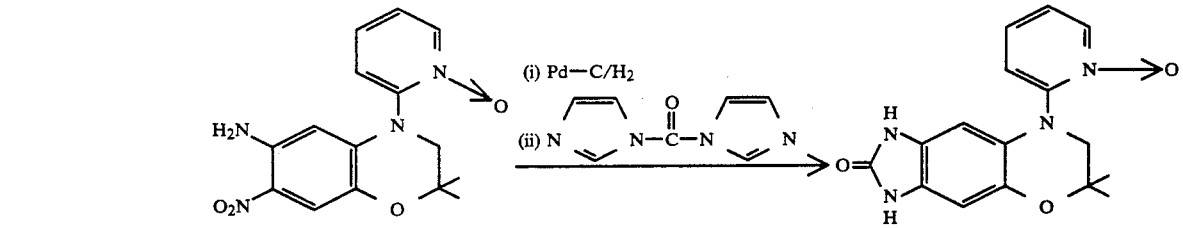

To a solution of 632 mg 2-(6-amino-3,4-dihydro-2,2-dimethyl-7-nitro-2H-1,4-benzoxazin-4-yl)pyridine 1-oxide in 10 ml acetic acid, was added 50 mg of 10% palladium carbon, and catalytic hydrogenation was performed. The reaction mixture was filtered by the use of Celite, the solvent was distilled off from the filtrate under reduced pressure, the residue was dissolved in 10 ml tetrahydrofuran, 5 ml tetrahydrofuran solution containing 324 mg carbonyldiimidazole was added under ice cooling, and the mixture was stirred overnight at room temperature. The precipitate which separated out was filtered off, the solvent was distilled off from the filtrate under reduced pressure, the residue thus obtained was dissolved in water, the aqueous solution was washed with chloroform and allowed to stand at room temperature for one hour, and the crystals which separated out were collected by filtration, thus giving 130 mg of 2-(7,8-dihydro-6,6-dimethyl-2-oxo-6H-[1,4]oxazino[2,3-f]benzimidazolin-8-yl)pyridine 1-oxide.

This compound has the physicochemical properties as shown below.

i) Melting point 220°-225° C.

ii) Elemental analysis (as $C_{16}H_{16}N_4O_3 \cdot H_2O$)

|  | C (%) | H (%) | N (%) |
|---|---|---|---|
| Calcd. | 58.17 | 5.49 | 16.96 |
| Found | 57.89 | 5.39 | 16.88 | iii) NMR spectrum (CDCl$_3$): δ(ppm): 1.32 (6H, s), 3.80 (2H, brs), 6.18 (1H, s), 6.36 (1H, s), 6.8-7.0 (1H, m), 7.2-7.4 (2H, m), 8.2-8.4 (1H, m), 9.95 (1H, s), 10.11 (1H, s)

EXAMPLE 7

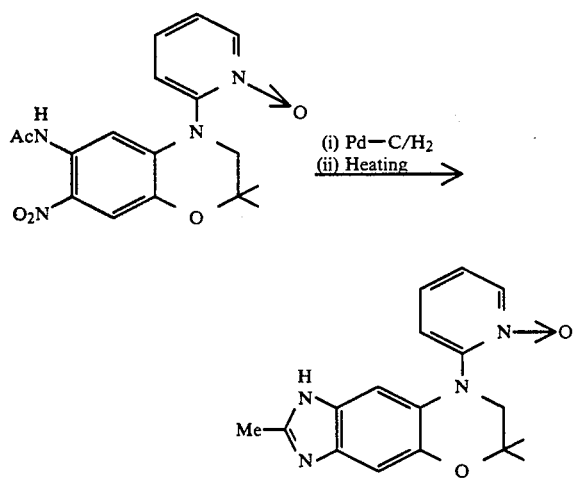

To a solution of 500 mg 2-(6-acetamido-3,4dihydro-2,2-dimethyl-7-nitro-2H-1,4-benzoxazin-4-yl)pyridine 1-oxide in 10 ml acetic acid, was added 40 mg 10% palladium-carbon to perform catalytic hydrogenation, the reaction mixture was filtered by the use of Celite, and the filtrate was stirred at 100° C. for 30 minutes. After cooling, the solvent was distilled off under reduced pressure, the rest was neutralized by addition of a saturated aqueous solution of sodium bicarbonate and extracted with chloroform, the extract was washed with water and dried over anhydrous magnesium sulfate, and the solvent was distilled off from the dried solution under reduced pressure. The residue thus obtained was purified by column chromatography on silica gel (elutant: 1:1 mixture of chloroform and methanol), and further recrystallized from ethanol-isopropyl ether, thus giving 180 mg of 2-(7,8-dihydro-2,6,6-trimethyl-6H-[1,4]oxazino[2,3-f]benzimidazol-8-yl)pyridine 1-oxide.

This compound has the physicochemical properties as shown below.

i) Melting point 165°-170° C.

ii) NMR spectrum (CDCl$_3$): δ(ppm): 1.32 (6H, s), 2.52 (3H, s), 3.80 (2H, s), 6.80 (1H, s), 6.9-7.5 (4H, m), 8.2-8.3 (1H, m)

EXAMPLE 8

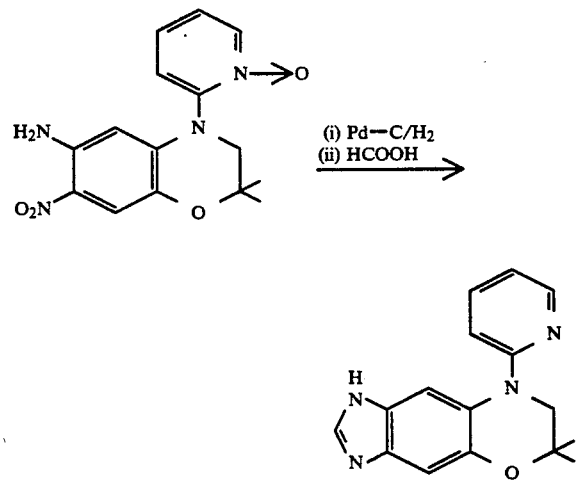

To a solution of 500 mg 2-(6-amino-3,4-dihydro-2,2-dimethyl-7-nitro-2H-1,4-benzoxazin-4-yl)pyridine 1-oxide in 25 ml acetic acid, was added a catalytic amount of 10% palladium-carbon to perform catalytic hydrogenation. The catalyst was filtered off from the reaction mixture, the solvent was distilled off from the filtrate under reduced pressure, the residue was dissolved in 10 ml formic acid, and the solution was heated under reflux for 18 hours with stirring. After distilling off the solvent from the reaction mixture, water was added to the residue, and the resulting mixture was neutralized by addition of sodium bicarbonate and extracted with ethyl acetate. The extract was washed with water and dried over anhydrous magnesium sulfate, the solvent was distilled off from the dried solution, the residue was subjected to column chromatography on silica gel, elution was conducted by the use of a 20:1 mixture of chloroform and methanol, and the crude product thus obtained was recrystallized from ethanol, thus giving 119 mg of 1,6,7,8-tetrahydro-6,6-dimethyl-8-(2-pyridyl)imidazo[4,5-g][1,4]benzoxazine.

This compound has the physicochemical properties as shown below.

i) Melting point 268°-271° C.

ii) Elemental analysis (as $C_{16}H_{16}N_4O$)

|  | C (%) | H (%) | N (%) |
|---|---|---|---|
| Calcd. | 68.55 | 5.75 | 19.99 |
| Found | 68.43 | 5.68 | 19.81 | iii) NMR spectrum (DMSO-d$_6$): δ(ppm): 1.22 (6H, s), 3.88 (2H, s), 6.8-6.9 (1H, m), 7.01 (1H, s), 7.35 (1H, d), 7.5-7.8 (2H, m), 8.03 (1H, s), 8.2-8.4 (1H, m), 12.05 (1H, brs)

EXAMPLE 9

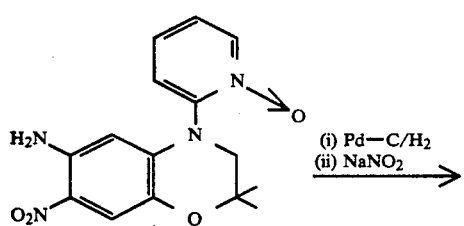

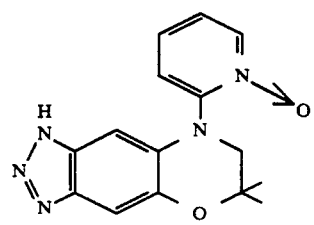

1) To a solution of 549 mg 2-(6-amino-3,4-dihydro-2,2-dimethyl-7-nitro-2H-1,4-benzoxazin-4-yl)pyridine N-oxide in 30 ml acetic acid, was added a catalytic amount of 10% palladium-carbon powder, and catalytic hydrogenation was performed at ordinary temperature and pressure. The catalyst was filtered off from the reaction mixture, and the solvent was distilled off from the filtrate, thus giving crude 2-(6,7-diamino-3,4-dihydro-2,2-dimethyl-2H-1,4-benzoxazin-4-yl)pyridine N-oxide. This product was immediately used for the succeeding reaction.

2) To a solution of 2-(6,7-diamino-3,4-dihydro-2,2-dimethyl-2H-1,4-benzoxazin-4-yl)pyridine N-oxide obtained above in a mixture of 0.5 ml acetic acid and 1 ml water, was added a solution of 139 mg sodium nitrite in 0.5 ml water at room temperature, the mixture was heated at 80° C. for one minute, and a solution of 0.52 g sodium hydroxide and 16 g sodium chloride in 70 ml water was added to the reaction mixture, followed by extraction with ethyl acetate. The extract was dried over anhydrous magnesium sulfate, the solvent was distilled off from the dried solution, the residue left was subjected to column chromatography on silica gel, and the crystals obtained by elution with a 10:1 mixture of chloroform and methanol were recrystallized from ethanol, thus giving 278 mg of 2-(1,6,7,8-tetrahydro[1,2,3]-triazolo[4,5-g][1,4]benzoxazin-8-yl)pyridine N-oxide. This compound has the physicochemical properties as shown below.

i) Melting point 262°–264.5° C.
ii) Elemental analysis (as $C_{15}H_{15}N_5O_2$)

|  | C (%) | H (%) | N (%) |
|---|---|---|---|
| Calcd. | 60.60 | 5.09 | 23.56 |
| Found | 60.58 | 5.09 | 23.59 | iii) NMR spectrum (DMSO-$d_6$): δ(ppm): 1.36 (6H, s), 3.61 (2H, s), 6.36 (0.5H, s), 6.73 (0.5H, s), 7.0–7.8 (4H, m), 8.3–8.4 (1H, m), 14.91 (0.5H, brs), 15.16 (0.5H, brs)

EXAMPLE 10

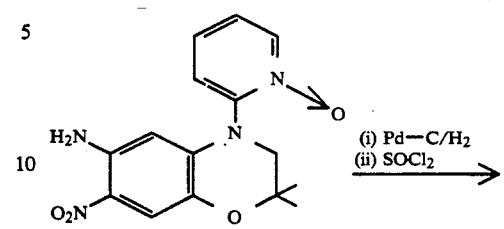

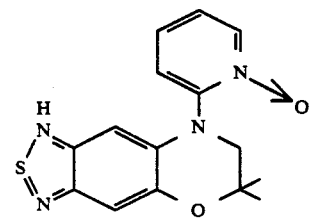

1) Catalytic hydrogenation of 603 mg 2-(6-amino-3,4-dihydro-7-nitro-2H-1,4-benzoxazin-4-yl)pyridine N-oxide was carried out in the same way as in Example 9-(1), and crude 2-(6,7-diamino-3,4-dihydro-2,2-dimethyl-2H-1,4-benzoxazin-4-yl)pyridine N-oxide thus obtained was immediately used for the succeeding reaction.

2) To a suspension of 2-(6,7-diamio-3,4-dihydro-2,2-dimethyl-2H-1,4-benzoxazin-4-yl)pyridine N-oxide obtained above in a mixture of 8 ml benzene and 2.1 ml triethylamine, was added dropwise slowly a solution of 0.36 ml thionyl chloride in 6 ml benzene, and the mixture was heated under reflux for 15 minutes, with stirring. The reaction mixture was poured into ice water, the resulting mixture was extracted with ethyl acetate, the extract was dried over anhydrous magnesium sulfate, and the solvents were distilled off from the dried solution. The residue was subjected to column chromatography on silica gel, elution was conducted by the use of a 2:1 mixture of chloroform-acetone, and amorphous substances (246 mg) were obtained. The amorphous substances were subjected to column chromatography on silica gel, elution was conducted by the use of a 70:1 mixture of chloroform and methanol. The crystals thus obtained were recrystallized from ethanol, giving 93 mg of 2-(7,8-dihydro-6,6-dimethyl-6H-[1,2,5]thiadiazolo[3,4-g][1,4]benzoxazin-8-yl)pyridine N-oxide.

This compound has the physicochemical properties as shown below.

i) Melting point 173°–174° C.
ii) Elemental analysis (as $C_{15}H_{14}N_4O_2S$)

|  | C (%) | H (%) | N (%) | S (%) |
|---|---|---|---|---|
| Calcd. | 57.31 | 4.49 | 17.82 | 10.20 |
| Found | 57.10 | 4.67 | 17.55 | 10.16 | iii) NMR spectrum (CDCl$_3$): δ(ppm): 1.51 (6H, s), 3.73 (2H, brs), 6.87 (1H, s), 7.2–7.6 (4H, m), 8.3–8.4 (1H, m)

Dosage Form Example

|                       | 1 mg tablet | 2 mg tablet |
|-----------------------|-------------|-------------|
| The Compound of Example 2 | 1 mg     | 2 mg        |
| Lactose               | 80          | 100         |
| Corn starch           | 34.4        | 42.2        |
| Hydroxypropylcellulose| 4           | 5           |
| Talc                  | 0.4         | 0.5         |
| Magnesium stearate    | 0.2         | 0.3         |
|                       | 120 mg      | 150 mg      |

Production method:

1 mg Tablet:

The compound of Example 2 (100 g), 8000 g of lactose and 3440 g of corn starch are mixed up homogeneously by using a fluidized granulating and coating apparatus.

Then, 400 g 10% hydroxypropylcellulose solution is added to be granulated. After drying, sieving (20 mesh) and adding thereto 40 g of talc and 20 g of magnesium stearate, the resulting mixture is tabletted using a rotary tabletting machine (7 mm×8.4R). 2 mg Tablet:

The compound of Example 2 (100 g), 5000 g of lactose and 2110 g of corn starch are mixed up homogeneously by using a fluidized granulating coating apparatus. Then, 2500 g of 10% hydroxypropylcellulose solution is added to be granulated. After drying, sieving (20 mesh) and adding thereto 25 g of talc and 15 g of magnesium stearate, the resulting mixture is tabletted using a rotary tabletting machine (7.5 mm×9R).

REFERENCE EXAMPLE 3

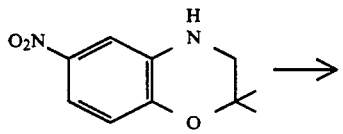

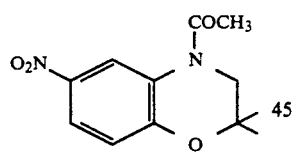

A mixture of 20 g 3,4-dihydro-2,2-dimethyl-6-nitro-2H, 1,4-benoxazine, 40 ml acetic anhydride and 40 ml pyridine was heated at 60° C. for 70 hours with stirring, the reaction mixture was poured into water, and the precipitate which separated out was collected by filtration and recrystallized from 240 ml ethanol, giving 21.4 g of 4-acetyl-3,4-dihydro-2,2-dimethyl-6-nitro-2H-1,4-benzoxazine. 500 mg of the crystals thus obtained were further recrystallized from 6 ml ethanol, giving 394 mg of a sample for analysis.

This compound has the following physicochemical properties:

i) Melting point 126.5°–129.5° C.

ii) Elemental analysis (as $C_{12}H_{14}N_2O_4$)

|        | C (%) | H (%) | N (%) |
|--------|-------|-------|-------|
| Calcd. | 57.59 | 5.64  | 11.19 |
| Found  | 57.52 | 5.57  | 11.22 | iii) NMR spectrum (CDCl$_3$): δ(ppm): 1.39 (6H, s), 2.40 (3H, s), 3.75 (2H, s), 6.94 (1H, d}, 7.97 (1H, dd), 8.94 (1H, brs)

REFERENCE EXAMPLE 4

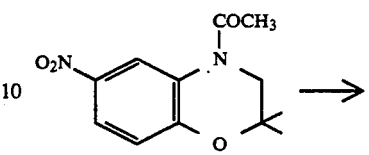

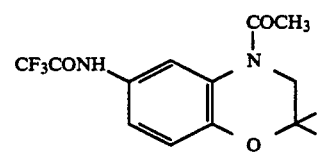

1) To a suspension of 20.9 g 4-acetyl-3,4-dihydro-2,2-dimethyl-6-nitro-2H-1,4-benzoxazine in 200 ml ethanol, was added a catalytic amount of Raney nickel, and the catalytic hydrogenation was carried out at ordinary temperature and pressure. The catalyst was filtered off from the reaction mixture, and the solvent was distilled off from the filtrate, giving 18.2 g of crude 4-acetyl-6-amino-3,4-dihydro-2,2-dimethyl-2H-1,4-benzoxazine.

2) To a mixture of 18.2 g 4-acetyl-6-amino-3,4-dihydro-2,2-dimethyl-2H-1,4-benzoxazine obtained above, 120 ml methylene chloride and 13.8 ml triethylamine, was added dropwise under ice cooling a solution of 13.7 ml trifluoroacetic anhydride in 40 ml methylene chloride over a period of 20 minutes, and the resulting mixture was stirred for one hour under ice cooling. To the reaction mixture, was added 100 ml water with stirring, the aqueous layer was extracted with chloroform, the two organic layers were put together, the combined organic solution was dried over anhydrous magnesium sulfate, the solvents were distilled off from the dried solution, and the residue was recrystallized from 60 ml ethanol, giving 22.1 g of 4-acetyl-3,4-dihydro-2,2-dimethyl-6-trifluoroacetylamino-2H-1,4-benzoxazine.

This compound has the following physicochemical properties:

i) Melting point 162°–164° C.

ii) Elemental analysis (as $C_{14}H_{15}F_3N_2O_3$)

|        | C (%) | H (%) | N (%) | F (%) |
|--------|-------|-------|-------|-------|
| Calcd. | 53.17 | 4.78  | 8.86  | 18.02 |
| Found  | 53.01 | 4.69  | 8.84  | 17.84 | iii) NMR spectrum (CDCl$_3$): δ(ppm): 1.34 (6H, s), 2.37 (3H, s), 3.69 (2H, s), 6.86 (1H d), 7.27 (1H, brs), 7.89 (1H, brs), 8.52 (1H, brs)

REFERENCE EXAMPLE 5

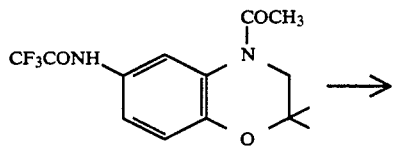

-continued

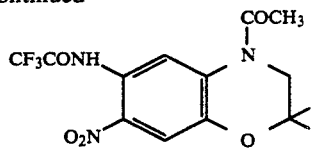

To a solution of 22.0 g 4-acetyl-3,4-dihydro-2,2-dimethyl-6-trifluoroacetylamino-2H-1,4-benzoxazine in 100 ml acetic acid, was added dropwise a solution of 3.7 ml fuming nitric acid in 50 ml acetic acid, and the resulting solution was stirred at room temperature for two hours. The reaction mixture was poured into 600 ml ice water, the crystals which separated out were collected by filtration, and recrystallized from 100 ml ethanol, giving 21.6 g of 4-acetyl-3,4-dihydro-2,2-dimethyl-7-nitro-6-trifluoroacetylamino-2H-1,4-benzoxazine.

This compound has the following physicochemical properties.
i) Melting point 130°–137° C.
ii) Elemental analysis (as $C_{14}H_{14}F_3N_3O_5$)

|  | C (%) | H (%) | N (%) | F (%) |
|---|---|---|---|---|
| Calcd. | 46.54 | 3.91 | 11.63 | 15.78 |
| Found | 46.50 | 3.89 | 11.62 | 15.72 | iii) NMR spectrum (CDCl$_3$): δ(ppm): 1.37 (6H, s), 2.48 (3H, s), 3.77 (2H, s), 7.83 (1H, s), 8.86 (1H, s), 11.20 (1H, brs)

REFERENCE EXAMPLE 6

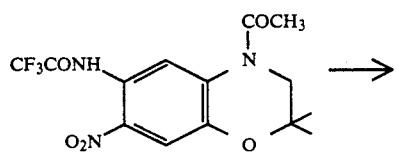

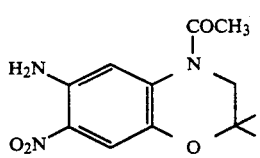

A mixture of 21.6 g 4-acetyl-3,4-dihydro-2,2-dimethyl-7-nitro-6-trifluoroacetylamino-2H-1,4-benzoxazine, 500 ml methanol, 50 ml water and 10.5 g sodium bicarbonate was stirred at room temperature for seven hours, the reaction mixture was poured into 1.5 l ice water, and the precipitate which separated out was collected by filtration and recrystallized from 450 ml ethanol, giving 13.5 g of 4-acetyl-6-amino-3,4-dihydro-2,2-dimethyl-7-nitro-2H-1,4-benzoxazine.

This compound has the following physicochemical properties:
i) Melting point 201.5°–204.5° C.
ii) Elemental analysis (as $C_{12}H_{15}N_3O_4$)

|  | C (%) | H (%) | N (%) |
|---|---|---|---|
| Calcd. | 54.33 | 5.70 | 15.84 |
| Found | 54.15 | 5.63 | 15.83 | iii) NMR spectrum (CDCl$_3$): δ(ppm): 1.37 (6H, s), 2.37 (3H, s), 3.65 (2H, s), 7.38 (1H, s), 7.64 (1H, s)

REFERENCE EXAMPLE 7

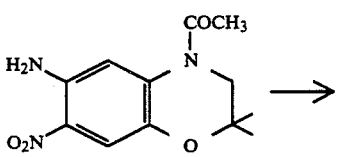

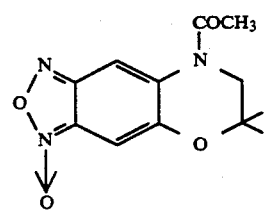

To a suspension of 530 mg 4-acetyl 6-amino-3,4-dihydro-2,2-dimethyl-7-nitro-2H-1,4-benzoxazine in 3 ml 5N HCl, was added dropwise 3 ml aqueous solution containing 156 mg sodium nitrite under ice cooling, the mixture was stirred for one hour under ice cooling, 1 ml aqueous solution containing 73 mg sodium nitrite was further added dropwise, and the resulting mixture was stirred for ten minutes. To the reaction mixture thus obtained, was added dropwise 3 ml aqueous solution containing 137 mg sodium azide under ice cooling, and the mixture was stirred for 90 minutes. After addition of 10 ml water, the precipitate which separated out was collected by filtration, and its solution in 5 ml toluene was heated under reflux for eight hours. The reaction mixture was diluted with ethyl acetate, the diluted solution was dried over anhydrous magnesium sulfate, and the solvents were distilled off from the dried solution. The residue was subjected to column chromatography on silica gel, the crystals obtained by elution with a 50:1 mixture of chloroform and ethyl acetate were recrystallized from 14 ml ethanol, giving 267 mg of 8-acetyl-7,8-dihydro-6,6-dimethyl-6H-[1,2,5]oxadiazolo[3,4-g][1,4]benzoxazine 3-oxide.

This compound has the following physicochemical properties:
i) Melting point 168°–170.5° C.
ii) Elemental analysis (as $C_{12}H_{13}N_3O_4$)

|  | C (%) | H (%) | N (%) |
|---|---|---|---|
| Calcd. | 54.75 | 4.98 | 15.96 |
| Found | 54.61 | 4.91 | 15.98 | iii) NMR spectrum (CDCl$_3$): δ(ppm): 1.41 (6H, s), 2.43 (3H, s), 3.80 (2H, s), 6.79 (1H, s), 7.72 (1H, s)

REFERENCE EXAMPLE 8

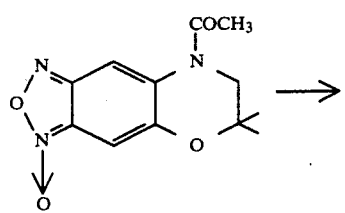

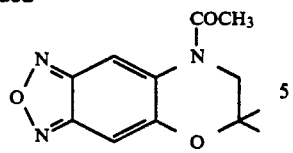

A mixture of 211 mg 8-acetyl-7,8-dihydro-6,6-dimethyl-6H-[1,2,5]oxadiazolo[3,4-g][1,4]benzoxazine 3-oxide, 15 ml toluene and 0.18 ml triethyl phosphite was heated under reflux for 16 hours, the solvent was distilled off from the reaction mixture, diethyl ether was added to the residue, and the precipitate was collected by filtration and recrystallized from 2 ml ethanol, giving 136 mg of 8-acetyl-7,8-dihydro-6,6-dimethyl-6H-[1,2,5]oxadiazolo[3,4-g][1,4]benzoxazine.

This compound has the following physicochemical properties:

i) Melting point 142°-144° C.
ii) Elemental analysis (as $C_{12}H_{13}N_3O_3$)

|       | C (%) | H (%) | N (%) |
|-------|-------|-------|-------|
| Calcd. | 58.29 | 5.30 | 16.99 |
| Found  | 58.32 | 5.26 | 17.00 | iii) NMR spectrum (CDCl$_3$): δ(ppm): 1.42 (6H, s), 2.45 (3H, s), 3.86 (2H, s), 7.09 (1H, s), 7.9 (1H, brs)

REFERENCE EXAMPLE 9

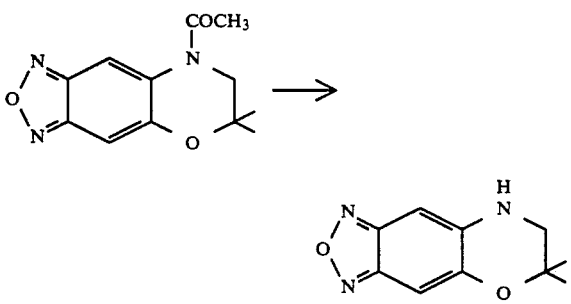

A mixture of 1.22 g 8-acetyl-7,8dihydro-6,6-dimethyl-6H-[1,2,5]oxadiazolo[3,4-g][1,4]benzoxazine, 40 ml methanol, 4 ml water and 1.37 g potassium carbonate was stirred at room temperature for one hour, the reaction mixture was poured into 300 ml ice water, and the resulting mixture was extracted with ethyl acetate. The extract was dried over anhydrous magnesium sulfate, the solvents were distilled off from the dried solution, and the residue was subjected to column chromatography on silica gel. Elution was conducted by the use of a 2:1 mixture of hexane and ethyl acetate, giving 1.02 g of 7,8-dihydro-6,6-dimethyl-6H-[1,2,5]oxadiazolo[3,4-g][1,4]benzoxazine.

This compound has the following physicochemical properties:

i) Melting point 148°-152.5° C.
ii) Elemental analysis (as $C_{10}H_{11}N_3O_2$)

|       | C (%) | H (%) | N (%) |
|-------|-------|-------|-------|
| Calcd. | 58.53 | 5.40 | 20.48 |
| Found  | 58.32 | 5.42 | 20.52 | iii) NMR spectrum (CDCl$_3$): δ(ppm): 1.43 (6H, s), 3.27 (3H, s), 4.77 (1H, brs), 6.53 (1H, s), 6.95 (1H, s)

EXAMPLE 11

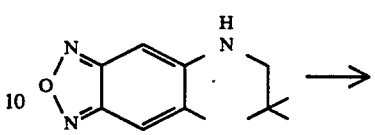

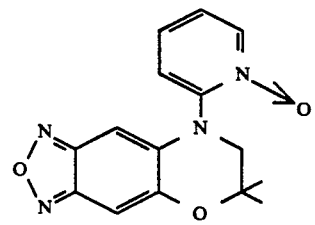

To a suspension of 215 mg sodium hydride (60%) in 5 ml hexamethylphosphoramide, were added 500 mg 7,8-dihydro-6,6-dimethyl-6H-[1,2,5]oxadiazolo[3,4-g][1,4]benzoxazine and 486 mg 2-chloropyridine N-oxide hydrochloride in that order, and the mixture was stirred at room temperature for six hours. The reaction mixture was poured into ice water, the resulting mixture was extracted with ethyl acetate, the extract was washed with an aqueous solution of sodium chloride and dried over anhydrous magnesium sulfate, and the solvents were distilled off from the dried solution. The residue was subjected to column chromatography on silica gel, and the crystals obtained by elution with a 2:1 mixture of chloroform and acetone were recrystallized from 6 ml ethanol, giving 409 mg of 2-(7,8-dihydro-6,6-dimethyl-6H-[1,2,5]oxadiazolo[3,4-g][1,4]benzoxazin-8-yl)pyridine 1-oxide.

This compound has the following physicochemical properties:

i) Melting point 193°-195° C.
ii) Elemental analysis (as $C_{15}H_{14}N_4O_3$)

|       | C (%) | H (%) | N (%) |
|-------|-------|-------|-------|
| Calcd. | 60.40 | 4.73 | 18.78 |
| Found  | 60.24 | 4.71 | 18.74 | iii) NMR spectrum (CDCl$_3$): δ(ppm): 1.51 (6H, s), 3.68 (2H, brs), 6.44 (1H, s), 7.09 (1H, s), 7.3-7.6 (3H, m), 8.3-8.5 (1H, m)

While the invention has been described in detail and with reference to specific embodiments thereof, it will be apparent to one skilled in the art that various changes and modifications can be made therein without departing from the spirit and scope thereof.

What is claimed is:

1. An oxazinobenzazole derivative of the formula (I):

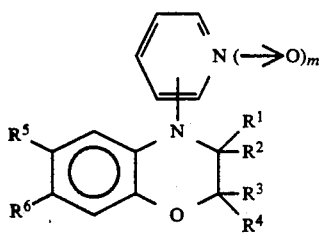

wherein R¹ and R² each represent a hydrogen atom, R³ and R⁴ each represents a hydrogen atom or a lower alkyl group; R⁵ and R⁶ jointly form a member selected from the group consisting of:

(a)

(b)

(c)

(d)

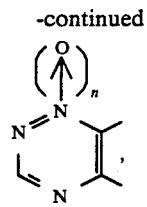

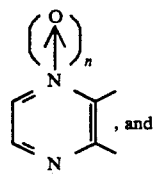

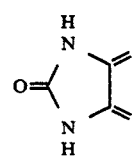

wherein n is 0 or 1, R is hydrogen, hydroxy, or an alkyl group; and m is an integer of 0 or 1.

2. The compound according to claim 1 which is selected from the group consisting of 7,8-dihydro-6,6-dimethyl-8-(2'-pyridyl)-6H-[1,4]oxazino[2,3-f][2,1,3]-benzoxadiazole 1,1'-dioxide or a pharmaceutically acceptable salt thereof; 2-(7,8-dihydro-6,6-dimethyl-6H-[1,4]oxazino[2,3-f][2,1,3]benzoxadiazol-8-yl)pyridine N-oxide or a pharmaceutically acceptable salt thereof; 7,8-dihydro-6,6-dimethyl-8-(2-pyridyl)-6H-[1,4]oxazino[ 2,3-f]benztriazole or a pharmaceutically acceptable salt thereof; 7,8-dihydro-6,6-dimethyl-8-(2'-pyridyl)-6H-[1,4]oxazino[2,3-f][2,1,3]benzoxadiazole 3,1'-dioxide or a pharmaceutically acceptable salt thereof; 2-(8,9-dihydro-7,7-dimethyl-7H-[1,4]oxazino[2,3-g]quinoxalin-9-yl)pyridine 1-oxide or a pharmaceutically acceptable salt thereof; 2-(7,8-dihydro-6,6-dimethyl-2-oxo-6H-[1,4]oxazino[2,3-f]benzimidazolin-8-yl)pyridine 1-oxide or a pharmaceutically acceptable salt thereof; 2-(7,8-dihydro-2,6,6-trimethyl-6H-[1,4]oxazino[2,3-f]benzimidazol-8-yl)pyridine 1-oxide or a pharmaceutically acceptable salt thereof; 1,6,7,8-tetrahydro-6,6-dimethyl-8-(2-pyridyl)imidazo[4,5-g][1,4]benzoxazine or a pharmaceutically acceptable salt thereof; 2-(1,6,7,8-tetrahydro[1,2,3]triazolo[4,5-g][1,4]benzoxazin-8-yl)pyridine N-oxide or a pharmaceutically acceptable salt thereof; and 2-(7,8-dihydro-6,6-dimethyl-6H-[1,2,5]-thiadiazolo[3,4-g][1,4]benzoxazin-8-yl)pyridine N-oxide or a pharmaceutically acceptable salt thereof.

3. A pharmaceutical composition containing at least one compound according to claim 1 and a pharmaceutically acceptable carrier.

4. A method of imparting an antispasmodic activity to a patient in need of such treatment, which comprises administering to said patient an anti-spasmodic effective amount of the pharmaceutical composition of claim 3.